United States Patent [19]

Verrier et al.

[11] Patent Number: 5,148,812
[45] Date of Patent: Sep. 22, 1992

[54] NON-INVASIVE DYNAMIC TRACKING OF CARDIAC VULNERABILITY BY ANALYSIS OF T-WAVE ALTERNANS

[75] Inventors: Richard L. Verrier, Bethesda; Bruce D. Nearing, Rockville, both of Md.

[73] Assignee: Georgetown University, Washington, D.C.

[21] Appl. No.: 768,054

[22] Filed: Sep. 30, 1991

Related U.S. Application Data

[63] Continuation-in-part of Ser. No. 659,711, Feb. 20, 1991, abandoned.

[51] Int. Cl.$^5$ .......................................... A61B 5/0452
[52] U.S. Cl. .................................................. 128/704
[58] Field of Search ............................... 128/702–704, 128/710; 346/413.06

[56] References Cited

U.S. PATENT DOCUMENTS

| | | | |
|---|---|---|---|
| 3,215,136 | 11/1965 | Holten et al. | 128/702 |
| 3,554,187 | 1/1971 | Glassner et al. | 128/703 |
| 4,023,564 | 5/1977 | Valiquette et al. | 128/704 |
| 5,046,504 | 9/1991 | Albert et al. | 128/702 |

Primary Examiner—William E. Kamm
Attorney, Agent, or Firm—Sterne, Kessler, Goldstein & Fox

[57] ABSTRACT

A non-invasive method for dynamic tracking of cardiac vulnerability to ventricular fibrillation is disclosed. A heart is monitored to sense an ECG signal. The sensed ECG signal is then amplified and low-pass filtered before it is digitally sampled and stored. The location of the T-wave in each R-R interval (pulse) of the ECG is estimated and each T-wave is partitioned into a plurality of time divisions. The sampled ECG signal in each of the time divisions is summed together and a time series is formed for each of the time divisions such that each time series includes corresponding sums from corresponding time divisions from successive T-waves. Each time series is detrended in order to eliminate the effects of drift and DC bias, and then a method of dynamic estimation is performed on each time series to estimate the amplitude of alternation for each time division. The methods of dynamic estimation include Complex Demodulation, Estimation by Subtraction, Least Squares Estimation, Auto Regressive Estimation, and Auto Regressive Moving Average Estimation. In this manner, the cycle-to-cycle alternation in the T-wave of the ECG can be determined for dynamic tracking of cardiac vulnerability. In one embodiment of the invention, the ECG is sensed non-invasively via the precordial or chest leads. In alternate embodiments, the ECG is sensed via a catheter inserted into the apex of either the left or right ventricles of the heart.

28 Claims, 13 Drawing Sheets

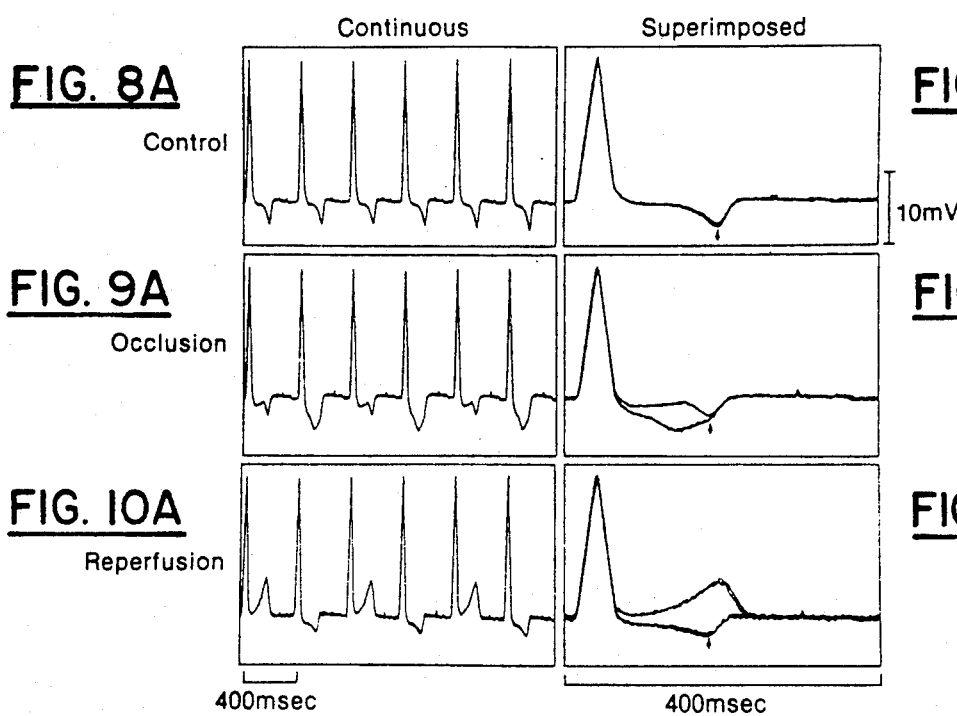
FIG. 8A Control — FIG. 8B
FIG. 9A Occlusion — FIG. 9B
FIG. 10A Reperfusion — FIG. 10B
Continuous / Superimposed
400msec / 400msec
10mV
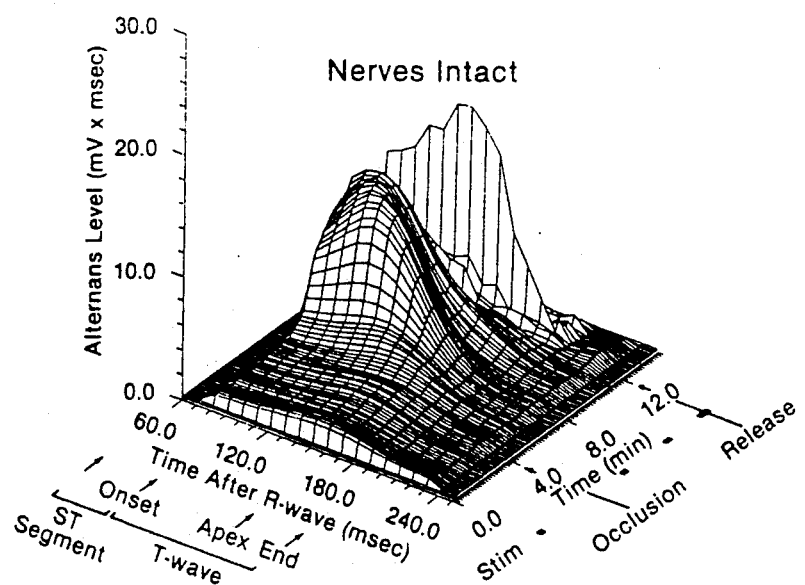
FIG. 11A
Nerves Intact

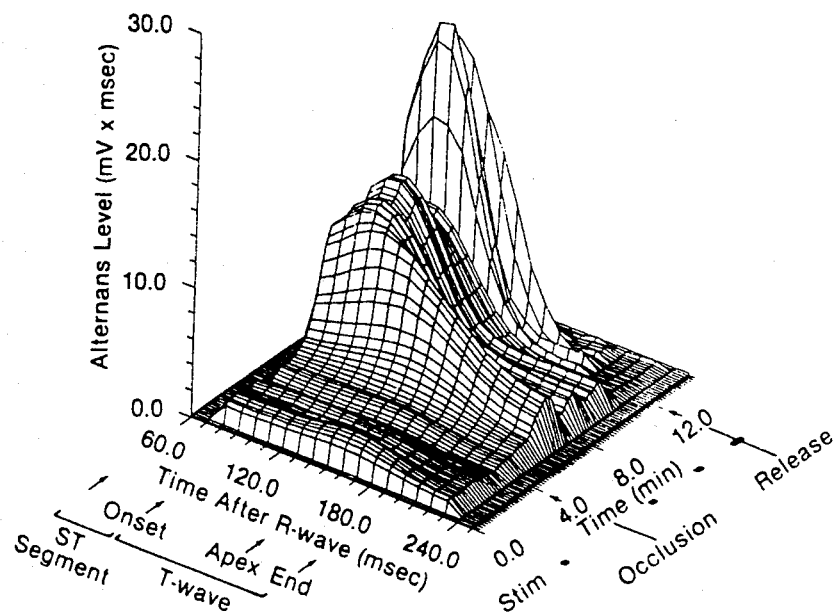
FIG. IIC
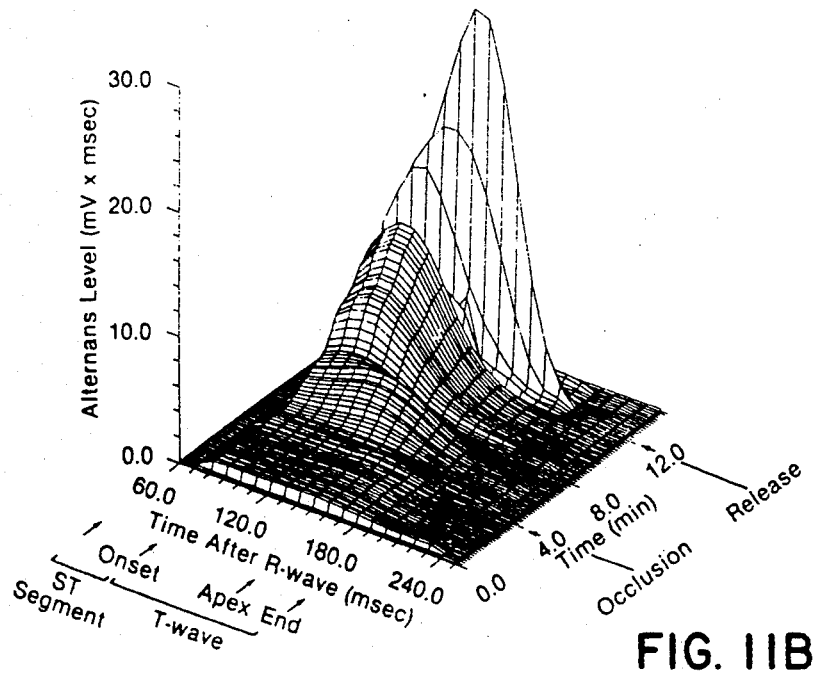
FIG. IIB

Correlation Between T-wave Alternans Level And Occurrence Of Ventricular Fibrillation During Coronary Artery Occlusion in the Dog

LEAD II (CONTINUOUS)

LEAD II (SUPERIMPOSED)

PRECORDIAL (V5) (CONTINUOUS)

PRECORDIAL (V5) (SUPERIMPOSED)

LEFT VENTRICULAR
INTRACAVITARY (CONTINUOUS)

LEFT VENTRICULAR
INTRACAVITARY (SUPERIMPOSED)

NON-INVASIVE DYNAMIC TRACKING OF CARDIAC VULNERABILITY BY ANALYSIS OF T-WAVE ALTERNANS

STATEMENT AS TO RIGHTS TO INVENTIONS MADE UNDER FEDERALLY SPONSORED RESEARCH AND DEVELOPMENT

Part of the work performed during development of this invention utilized U.S. Government funds. The U.S. Government has certain rights in this invention.

BACKGROUND OF THE INVENTION

1. Related Application

This application is a continuation-in-part of application Ser. No. 07/659,711; filed Feb. 20, 1991, now abandoned.

2. Field of the Invention

The invention relates to cardiology. More specifically, the invention relates to non-invasive identification and management of individuals at risk for sudden cardiac death. Cardiac vulnerability to ventricular fibrillation, the mode of sudden death, is dynamically tracked by analysis of alternans in the T-wave and ST segment of an electrocardiogram.

3. Background of the Invention

Sudden cardiac death, which claims over 350,000 lives annually in the United States, results from abrupt disruption of heart rhythm primarily due to ventricular fibrillation. Fibrillation occurs when transient neural triggers impinge upon an electrically unstable heart causing normally organized electrical activity to become disorganized and chaotic. Complete cardiac dysfunction results.

The first step in preventing sudden cardiac death is identifying those individuals whose hearts are electrically unstable. This is a major objective in cardiology. If vulnerable individuals can be reliably identified non-invasively, then prevention will be aided. Mass screening will become possible, and pharmacologic management of vulnerable individuals can be tailored to prevent ventricular fibrillation.

Programmed cardiac electrical stimulation has been used in patients to provide quantitative information on susceptibility and on the effectiveness of their pharmacologic therapy. Unfortunately, this method requires cardiac catheterization and introduces the hazard of inadvertent induction of ventricular fibrillation. Therefore, it is used only in severely ill patients and is performed only in hospitals. It is unsuitable for mass screening.

A technique which has shown great promise is that of analyzing alternans in the T-wave of an electrocardiogram (ECG). As used throughout this disclosure, the term "T-wave" is defined to mean the portion of an ECG which includes both the T-wave and the ST segment. Alternans in the T-wave results from different rates of re-polarization of the muscle cells of the ventricles. The extent to which these cells recover (or re-polarize) non-uniformly is the basis for electrical instability of the heart.

The consistent occurrence of alternans in the T-wave prior to fibrillation is well established. Thus, detection of alternans promises to be a useful tool in predicting vulnerability to fibrillation if an accurate method of quantifying the alternans were available. The following are examples of conventional attempts to quantify alternation in an ECG signal: Adam et al., "Fluctuations in T-Wave Morphology and Susceptibility to Ventricular Fibrillation," *Journal of Electrocardiology*, Vol. 17 (3), 209-218 (1984); Smith et al. "Electrical Alternans and Cardiac Electrical Instability," *Circulation*, Vol. 77, No. 1, 110-121 (1988); U.S. Pat. No. 4,732,157 to Kaplan et al.; and U.S. Pat. No. 4,802,491 to Cohen et al..

Smith et al. and Cohen et al. disclose methods for assessing myocardial electrical instability by power spectrum analysis of the T-wave. These methods derive an alternating ECG morphology index from a series of heartbeats. Sample point matrices are constructed and the alternating energy at each of the sample points is computed using the analytical method of multi-dimensional power spectral estimation which is calculated by constructing the discrete Fourier transform of the Hanning-windowed sample auto-correlation function. The alternating energy over the entire set of sample points is summed to generate the total alternating energy and then normalized with respect to the average waveform to produce an "alternating ECG morphology index (AEMI)."

While a powerful tool, Fourier power spectrum analysis averages time functions over the entire time series so that rapid arrhythmogenic changes, such as those due to neural discharge and reperfusion, are not detected because data from these events are intrinsically non-stationary.

Kaplan et al. disclose a method for quantifying cycle-to-cycle variation of a physiologic waveform such as the ECG for the purpose of assessing myocardial electrical stability. A physiologic waveform is digitized and sampled and a scatter plot of the samples is created. Non-linear transformation of the sample points determines a single parameter which attempts to quantify the degree of alternation in the sampled waveform and which is associated with the susceptibility of the physiologic waveform to enter into an aperiodic or chaotic state. Kaplan et al. suggest that "measurement of [this parameter] may provide an index of ECG waveform variability which may provide an improved correlation with susceptibility to ventricular fibrillation than previously available indices." See col. 3, lines 15-19. Whether ventricular fibrillation is a chaotic state, however, is still very much in debate. See Kaplan DT and Cohen RJ, "Searching for Chaos in Fibrillation," *Ann. N.Y. Acad. Sci.*, Vol. 591, pp. 367-374, 1990.

Adam et al. disclose a non-invasive method which involves spectral analysis of the alternation from beat-to-beat morphology of the ECG complex. The alternation of T-wave energy from beat-to-beat was measured to generate a T-wave alternation index (TWAI). This technique, however, is unable to detect alternation in waveform morphology which results in alternating wave shapes of equal energy. In addition, the amount of alternation detected per this method is dependent on the static portion of the wave shape. That is, the same amount of alternation superimposed on a different amplitude signal will result in different values for the T-wave alternation index such that this technique could completely obscure the presence of alternation in the original waveform morphologies.

Shin et al., "Assessment of Autonomic Regulation of Heart Rate Variability by the Method of Complex Demodulation," *IEEE Transactions on Biomedical Engineering*, Vol. 36, No. 2, February 1989, teaches a method to assess the influence of autonomic nervous system activity during behavioral stress. Shin et al. use the technique of complex demodulation to analyze the pattern of beat-to-beat intervals to determine the relative activity of the sympathetic and parasympathetic nervous systems. While Shin et al. exploited the dynamic analytical characteristics of complex demodulation, they did not analyze the morphology of the electrocardiogram and therefore did not acquire any information regarding cardiac vulnerability.

In the absence of an effective method for dynamically quantifying the magnitude of alternation, identification of alternans as a precursor of life-threatening arrhythmias and provision of a test for cardiac vulnerability have been unattainable. In addition, the conventional attempts to quantify alternans have employed inferior methods of alternans (i.e., ECG) sensing. The ECG signals used for the Cohen et al. analysis were sensed via epicardial (i.e., heart surface) electrodes or via lateral limb, rostral-caudal, and dorsal-ventral leads. Smith et al. sensed via leads I, a VF, and $V_{1-2}$. Adam et al. utilized ECG lead I "because in this lead the ratio of the amplitude of the pacing stimulus artifact to the amplitude of the QRS complex was usually smallest." See Adam et al. at 210. Lead I, however, provides only limited information regarding the electrophysiologic processes occurring in the heart.

There have been occasional reports in the human literature noting the presence of T-wave alternans in the precordial leads. However, there has been no suggestion of a superior lead configuration from the body surface which permits measurement of alternans as a quantitative predictor of susceptibility to ventricular fibrillation and sudden death. For example, alternans have been observed in precordial leads $V_4$ and $V_5$ during a PCTA (Percutaneous Transluminal Coronary Angioplasty) procedure on a fifty year-old man. M. Joyal et al., "ST-Segment Alternans During Percutaneous Transluminal Coronary Angioplasty," *Am. J. Cardiol.*, vol. 54, pp. 915–916 (1984). Similarly, alternans were noted in precordial leads $V_4$ through $V_6$ on a forty-four year-old man during and following a treadmill exercise. N. Belic, et al., "ECG Manifestations of Myocardial Ischemia," *Arch. Intern. Med.*, vol. 140, pages 1162–1165 (1980).

What is needed is a non-invasive, dynamic method for assessing vulnerability to ventricular fibrillation under diverse pathologic conditions relevant to the problem of sudden cardiac death. Among the most significant problems are enhanced discharge by the sympathetic nervous system, behavioral stress, acute myocardial ischemia, and reperfusion. To accommodate these conditions, the method must not assume stationarity of data and must be sensitive to slowly varying amplitude and phase over time. The diagnostic system must be sensitive to the fact that the area of injury to the heart can vary significantly, and the electrophysiologic end point to be detected must be fundamentally linked to cardiac vulnerability.

SUMMARY OF THE INVENTION

The present invention is a method and apparatus for non-invasive dynamic tracking of cardiac vulnerability to ventricular fibrillation. It is non-invasive as it detects vulnerability from leads placed on the surface of the chest. The method permits tracking of transient but deadly pathophysiologic events, such as enhanced discharge by the sympathetic nervous system, behavioral stress, acute myocardial ischemia and reperfusion.

A heart is monitored to sense an ECG signal. The sensed ECG signal is then amplified and low-pass filtered before it is digitally sampled and stored. The location of the T-wave in each R-R interval (heart beat) of the ECG is then estimated.

Next, each T-wave is partitioned into a plurality of time divisions. The sampled ECG signal in each of the time divisions is summed together and a time series is formed for each of the time divisions such that each time series includes corresponding time divisions from successive T-waves. The time series are detrended before further processing in order to remove the effects of drift and DC bias.

Dynamic estimation is performed on each time series to estimate the amplitude of alternation for each time division. The methods of dynamic estimation include Complex Demodulation, Estimation by Subtraction, Least Squares Estimation, Auto Regressive Estimation, and Auto Regressive Moving Average Estimation. The amplitude of alternation is used as an indication of cardiac susceptibility to ventricular fibrillation.

In one embodiment of the invention, the ECG is sensed non-invasively via the precordial or chest leads. Leads $V_5$ and/or $V_6$ detect the optimal alternans signal when the left side (the most common site of injury for the propagation of life-threatening arrhythmias) of the heart is ischemic or injured. Leads $V_1$ and/or $V_2$ are optimal for detecting obstruction of the right-sided coronary circulation. Additional precordial leads, such as $V_9$, may be useful for sensing alternans resulting from remote posterior wall injury. A physician may use the complete precordial lead system to obtain precise information non-invasively regarding the locus of ischemia or injury.

In alternate embodiments, the ECG is sensed via a catheter inserted into the apex of either the left or right ventricles of the heart.

BRIEF DESCRIPTION OF THE DRAWINGS

FIG. 8(*a*) is an ECG recorded within the left ventricle of a dog before coronary artery occlusion as set forth in the animal study below.

FIG. 8(*b*) shows superimposition of six successive beats from FIG. 8(*a*) presented on an expanded time scale.

FIG. 9(*a*) is an ECG recorded within the left ventricle of a dog after four minutes of coronary artery occlusion as set forth in the animal study below.

FIG. 9(*b*) shows superimposition of six successive beats from FIG. 9(*a*) presented on an expanded time scale.

FIG. 10(*a*) is an ECG recorded within the left ventricle of a dog after release of the coronary artery occlusion (during reperfusion) as set forth in the animal study below.

FIG. 10(b) shows superimposition of six successive beats from FIG. 10(a) presented on an expanded time scale.

FIG. 11(a) is a surface plot of the T-wave of the ECG for eight dogs with intact cardiac innervation showing the effects of coronary artery occlusion and reperfusion.

FIG. 11(b) is a surface plot of the T-wave of the ECG for six dogs after bilateral stellectomy showing the effects of coronary artery occlusion and reperfusion.

FIG. 11(c) is a surface plot of the T-wave of the ECG for eleven dogs during thirty seconds of stimulation of the ansa subclavia of the decentralized left stellate ganglion showing the effects of coronary artery occlusion and reperfusion.

DETAILED DESCRIPTION OF THE PREFERRED EMBODIMENT

Figure 1:
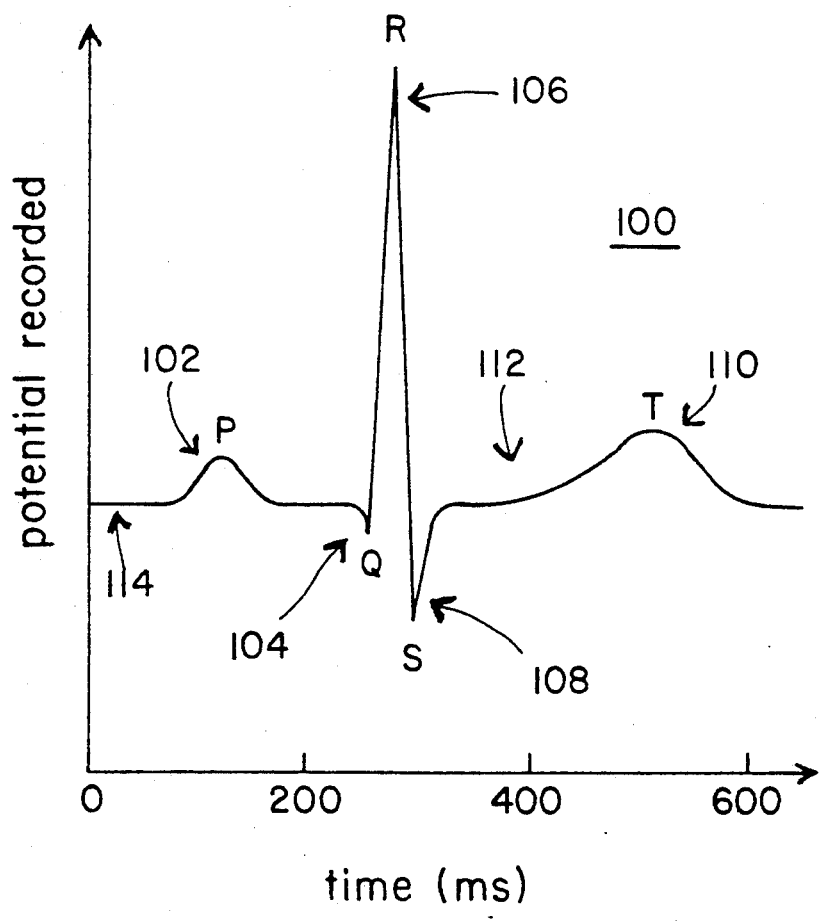
FIG. 1 is a typical ECG plot.

FIG. 1 shows a representative human surface ECG 100. A deflection 102 is known as the "P-wave" and is due to excitation of the atria. Deflections 104, 106 and 108 are known as the "Q-wave," "R-wave," and "S-wave," respectively, and result from excitation (depolarization) of the ventricles. Deflection 110 is known as the "T-wave" and is due to recovery (re-polarization) of the ventricles. One cycle (i.e., cardiac cycle or heart beat) of the ECG from the apex of a first R-wave to the apex of the next R-wave is known as the R-R interval.

A portion 112 between S-wave 108 and T-wave 110 of ECG 100 is known as the "ST segment". ST segment 112 includes the portion of the ECG from the end of S-wave 108 to the beginning of the T-wave 110. Because this invention is concerned with alternans in the ST segment as well as in the T-wave, the term "T-wave" in this disclosure, as noted above, includes both the T-wave and the ST segment portions of the ECG.

A more detailed discussion of ECG sensing and analysis is provided in Dale Dubin, *Rapid Interpretation of EKG's*, 4th Edition, COVER Publishing Company, 1990, which is expressly incorporated herein by reference.

The inventors have found that most alternans occurs in the first half of the T-wave, the period of greatest vulnerability to ventricular fibrillation. See, Nearing BD, Huang AH and Verrier RL, "Dynamic Tracking of Cardiac Vulnerability by Complex Demodulation of the T Wave," *Science* 252:437–440, 1991.

Method of the Invention

Figure 2:
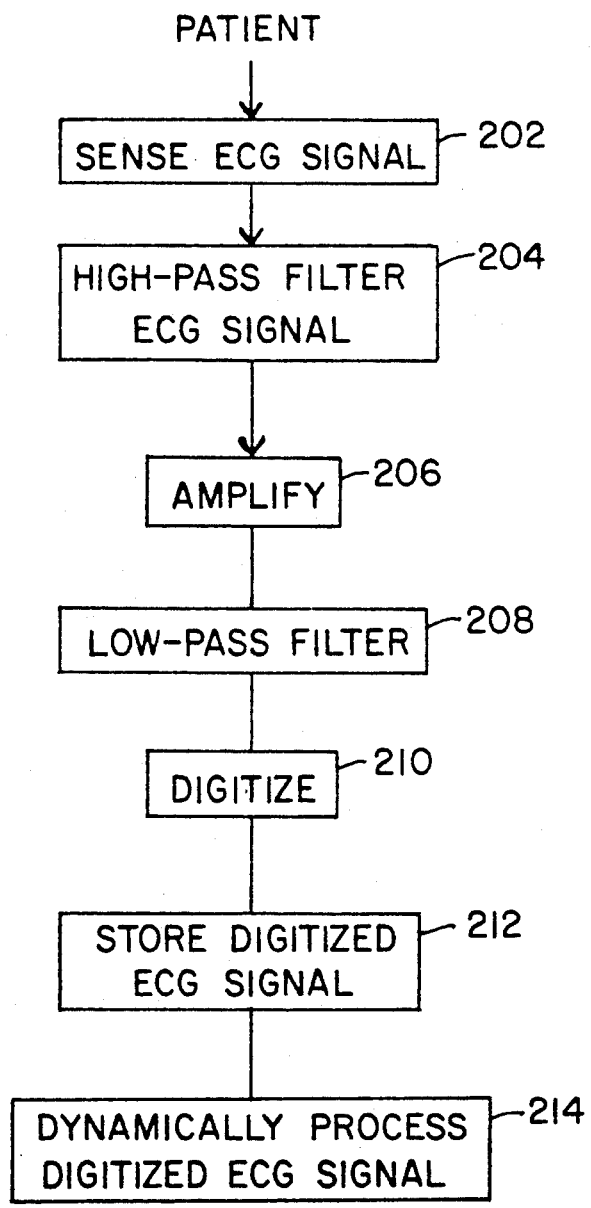
FIG. 2 is high-level block diagram of the method of the present invention.
Figure 3:
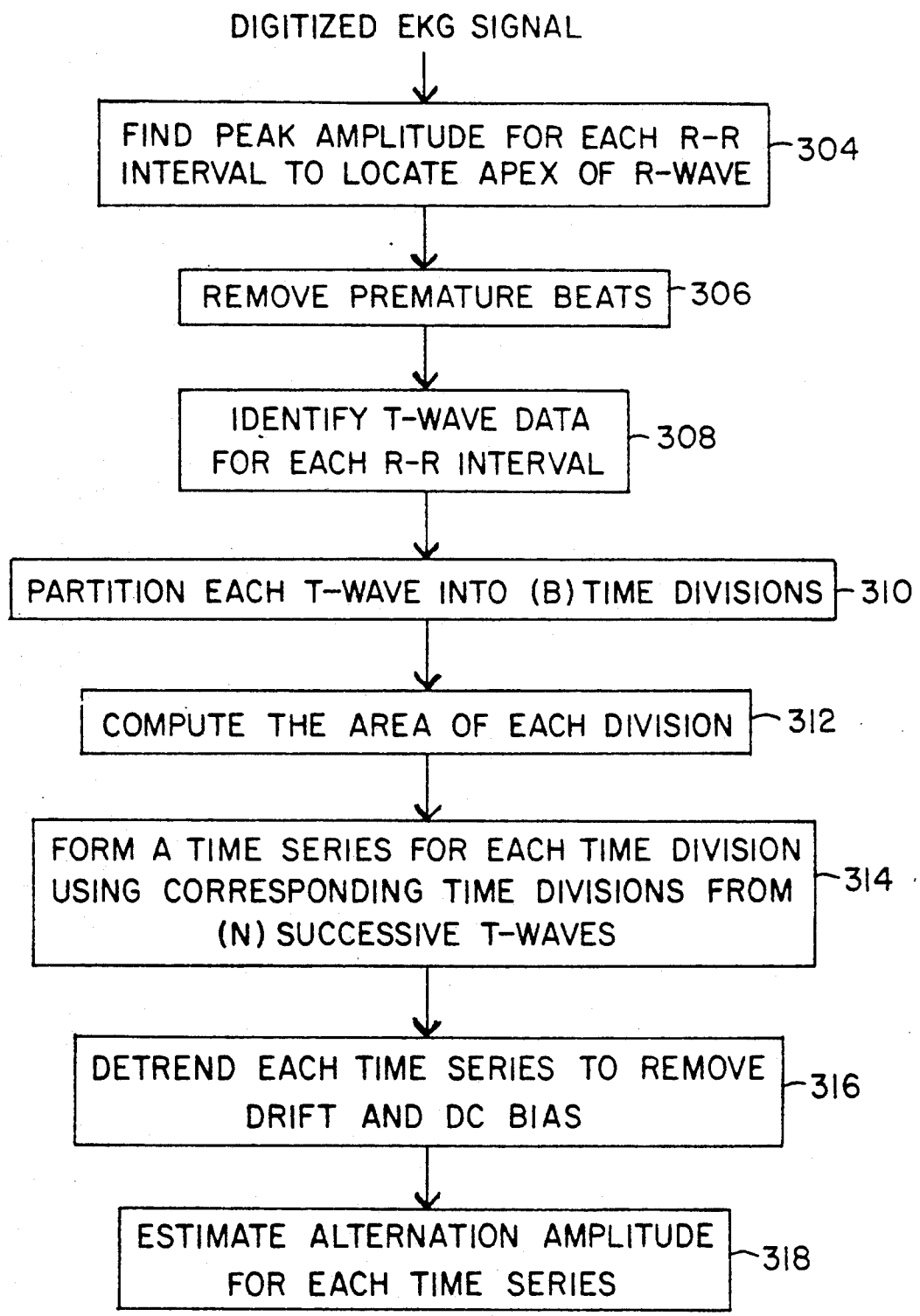
FIG. 3 is a flow chart detailing Step 214 of FIG. 2.
Figure 4:
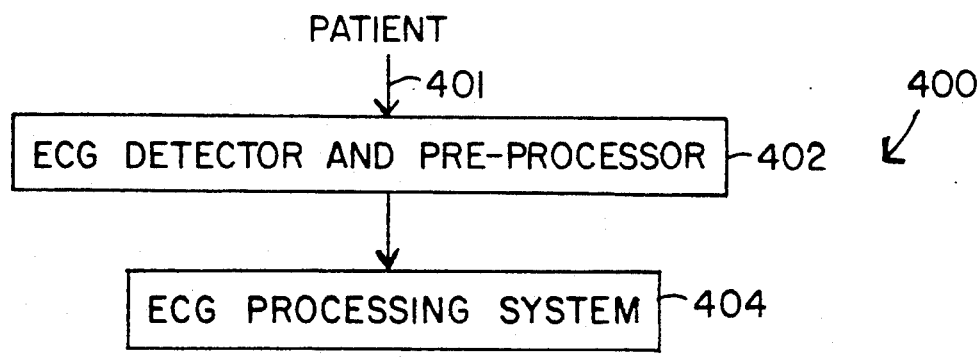
FIG. 4 is a high-level block diagram of the apparatus of the invention.
Figure 5:
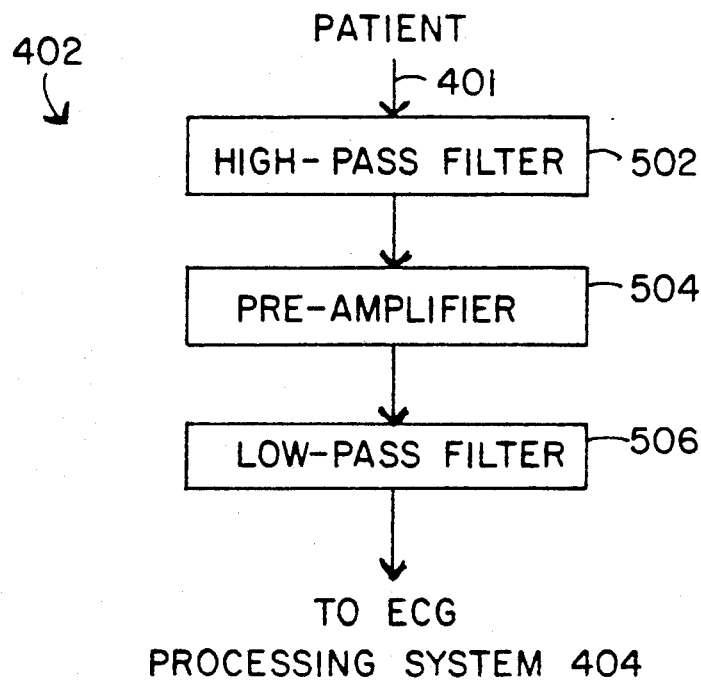
FIG. 5 is a detailed block diagram of ECG detector and pre-processor 402.

The method of the present invention for analyzing alternation in the T-waves of an ECG is now discussed with reference to FIGS. 2 and 3.

An ECG signal containing a plurality N of R-R intervals is sensed from a patient in real time at step 202. The preferred method of non-invasively sensing the ECG signal is discussed in detail below. Because the body is akin to a dipole, a large DC component will be present in the sensed ECG. This DC component is removed at step 204 with a high-pass filter prior to amplification of the ECG signal at step 206. The amplified ECG signal is then low-pass filtered at step 208 to limit the signal bandwidth before it is digitally sampled at step 210. The digitized data may then be stored on a magnetic or optical storage device at step 212. Finally, the digitized ECG data is dynamically processed to produce an estimation of alternans amplitude at step 214.

As an alternative to this real-time signal pre-processing, the ECG signal may be retrieved from the storage device (step 212) and processed (step 214) at a later, more convenient time.

Processing step 214 of the preferred embodiment of the invention is described in detail with reference to FIG. 3. At step 304, the apex of each R-wave in the signal data for each of the N beats is located by finding the peak amplitudes in the digitized signal. Premature beats are removed at step 306 by comparison of each R-R interval with fixed criteria. At step 308, a portion of the ECG corresponding to an estimated location (with respect to R-wave 106) of T-wave 110 is identified.

At step 310, the T-wave 110 and 112 portion of the ECG signal is partitioned into "B" time divisions, where "B" may include a single digital sample or a plurality of samples. The area between the ECG and the isoelectric baseline is computed for each time division, at step 312, by summing the areas of all samples in the time division. Then at step 314, "N" successive beats (e.g., from control through release in the animal experiments discussed below) are sequenced into a time series for each of the "B" time divisions:$(X(n), n=1,2,\ldots N)$.

A high-pass filter is used for detrending the time series at step 316 to remove the effects of drift and DC bias (e.g., high-pass filtering removes the large low-frequency variation in T-wave area that occurs during occlusion of a coronary artery). A cleaner signal is then available for dynamic estimation, which is performed at step 318 to estimate the amplitude of alternation for each time series.

The estimation of step 318 may be performed via several dynamic methods. By "dynamic" method, it is meant any analytical process sufficiently rapid to track (i.e., estimate) transient changes such as those which occur in alternans amplitude in response to physiologic and pathophysiologic processes triggering arrhythmias. These include, for example, enhanced neural discharge, acute myocardial ischemia and reperfusion. A "dynamic" method should be able to track alternans from as few as approximately ten heart beats (or less). This precludes analytic processes (e.g., Fourier power spectrum analysis) which require stationarity of data for several minutes. Specific, but not exclusive, examples of methods for dynamic estimation include:
1. Complex Demodulation,
2. Estimation by Subtraction,
3. Least Squares Estimation,
4. Auto-Regressive (AR) Estimation, and
5. Auto-Regressive Moving Average (ARMA) Estimation.

(a) Complex Demodulation

Complex demodulation is the preferred method of dynamic estimation of the beat-to-beat alternation in the amplitude of each time series. Complex demodulation is a type of harmonic analysis which provides a continuous measure of the amplitude and phase of an oscillation with slowly changing amplitude and phase. It detects features that might be missed or misrepresented by standard Fourier spectral analysis methods which assume stationarity of data.

By definition, alternans is a periodic alternation in the T-wave. The magnitude of alternans, however, changes slowly during a coronary artery occlusion and more rapidly during release, making it quasi-periodic. As such, it must be represented by a sinusoid with slowly varying amplitude, $A(n)$, and phase, $\phi(n)$:

$$X(n) = A(n) \cos[2\pi f_{ALT} T + \phi(n)]$$

where:

$X(n)$ = the data sequence with alternation in its amplitude $f_{ALT}$ = alternation frequency (Hz). It should be noted that this frequency is half of the heart rate.

Using the identity $$\cos(x) = \frac{e^{jx} + e^{-jx}}{2},$$

the equation for $X(n)$ can be rewritten as $$X(n) = A(n) \times \frac{(e^{j2\pi f_{ALT} Tn} e^{j\phi n} + e^{-j2\pi f_{ALT} Tn} e^{-j\phi n})}{2}$$

The method of complex demodulation requires multiplying this time series $X(n)$ by two times a complex exponential at the alternans frequency [to produce $Y_1(n)$] and then filtering the result to retain only the low frequency term $Y_2(n)$ as follows:

$$\begin{aligned} Y_1(n) &= X(n) \times 2e^{-j2\pi f_{ALT} Tn} \\ &= A(n)[e^{j\phi(n)} + e^{-j4\pi f_{ALT} Tn - j\phi(n)}] \\ Y_2(n) &= A(n) e^{j\phi(n)} \end{aligned}$$

The amplitude and phase of the alternans is then found from the filtered signal, $Y_2(n)$, as follows:

$$\begin{aligned} A(n) &= |Y_2(n)| \\ &= \text{magnitude of } Y_2(n) \\ &= \sqrt{Re[Y_2(n)]^2 + Im[Y_2(n)]^2} \end{aligned}$$

$$\begin{aligned} \phi(n) &= \text{phase of } Y_2(n) \\ &= \arctan\left[\frac{Im[Y_2(n)]}{Re[Y_2(n)]}\right] \end{aligned}$$

where: Im and Re refer to the imaginary and real parts of $Y_2$

For a more detailed discussion of complex demodulation, see *Fourier Analysis of Time Series: An Introduction* by Peter Bloomfield, John Wiley & Sons: New York, pp. 118-150; which is incorporated herein by reference.

(b) Estimation by Subtraction

The subtraction method of dynamic estimation is an alternative which may be substituted for complex demodulation. The subtraction method involves subtracting the area of each time division (n) of an R-to-R interval from the area of the corresponding time division of a subsequent (n+1), or alternatively, a previous (n−1) R-to-R interval to form a new time series $Y(n)$ representing the magnitude of alternans. Because this difference series $Y(n)$ may be positive or negative, the absolute value or magnitude of $Y(n)$ is used for the magnitude $A(n)$. That is:

$$\begin{aligned} Y(n) &= X(n) - X(n-1) \\ A(n) &= |Y(n)| \\ &= |X(n) - X(n-1)| \\ &= \text{magnitude of alternans} \end{aligned}$$

Some errors may be introduced into this estimate due to the slowly varying increase in magnitude of the T-wave size at the start of a coronary occlusion and the reduction in size following the occlusion. Also, some T-wave variation due to respiration is expected. Therefore detrending the sequence $X(n)$ using a high pass digital filter, or equivalent, improves the estimate by removing the effects of T-wave size changes. Also, averaging M samples together, where M is the number of beats occurring during a single respiratory cycle, aids in eliminating the respiratory effects on the estimate. Alternatively, the digital filter may remove both trends and respiratory changes if the respiration frequency is sufficiently different from the heart rate, so that the filtering does not alter the magnitude of the alternans estimate.

(c) Least Squares Estimation

The least squares estimation, which also turns out to be the maximum likelihood estimate in this case for estimating sinusoid amplitude in white noise, is a second alternative which may be substituted for complex demodulation to calculate a new sequence which is a dynamic estimate of the amplitude of alternans. Least squares estimation of the amplitude of alternans $A(n)$ for the data sequence $X(n)$ is derived as follows.

Assume for M points (e.g., 5 to 10 cardiac cycles) that:

$$X(n) = A \cos(2\pi f_{ALT} Tn) + N(n)$$

where:

$N(n)$ represents additive noise

In order to minimize the noise term and estimate the alternans component, create a new function T(A), where:

$$T(A) = \sum_{j=n}^{n+M-1} [X(j) - A\cos(2\pi f_{ALT}j)]^2$$

T(A) represents a measure of the difference between the model and the data. The best alternans magnitude estimate results if T(A) (i.e., the noise term) is minimized. To minimize T(A), take the derivative of T(A) with respect to A and set it equal to zero:

$$\frac{\delta T}{\delta A} = -2 \times \sum_{j=n}^{n+M-1} \{\cos(2\pi f_{ALT}j)[X(j) - A\cos(2\pi f_{ALT}j)]\} = 0$$

Next, solve this equation for A(n) (shown simply as "A" above) and take the absolute value of the result to yield the least squares estimate of the magnitude of the alternans:

$$A(n) = \frac{1}{M}\left|\sum_{j=n}^{n+M-1} [X(j)\cos(2\pi f_{ALT}j)]\right|$$

(d) Auto-Regressive Estimation (AR)

Auto-Regressive (AR) Estimation is a third method of dynamic estimation which may be substituted for complex demodulation. AR estimation models the alternans as follows:

$$X(n) = -\sum_{k=1}^{P} [a(k) \times X(n-k)] + u(n)$$

In this model, "P" is the number of auto regressive coefficients chosen for the estimation. u(n) represents noise and accounts for the imperfect fit of the estimation. The method of estimating the amplitude of alternans A(n) for the data sequence X(n) first involves calculating a matrix of co-variance coefficients c(i,k) according to the following formula:

$$c(i,k) = \frac{1}{M-P} \sum_{j=n+P}^{n+M-1} [X(j-i) \times X(j-k)]$$

where:
â = the best estimate of the true value of "a"
P = the number of auto regressive coefficients "â"
M = the number of cardiac cycles The co-variance coefficients are then used to form "P" auto regressive coefficients "â" as follows:

$$\begin{vmatrix} \hat{a}(1) \\ \hat{a}(2) \\ \cdot \\ \cdot \\ \cdot \\ \hat{a}(P) \end{vmatrix} = - \begin{vmatrix} c(1,1) & c(1,2) & \ldots & c(1,P) \\ c(2,1) & c(2,2) & \ldots & c(2,P) \\ \cdot & & & \\ \cdot & & & \\ \cdot & & & \\ c(P,1) & c(P,2) & \ldots & c(P,P) \end{vmatrix}^{-1} \times \begin{vmatrix} c(1,0) \\ c(2,0) \\ \cdot \\ \cdot \\ \cdot \\ c(P,0) \end{vmatrix}$$

The estimate of the alternans magnitude is then given by:

$$A(n) = \frac{\sigma^2}{1 - \sum_{n=1}^{P} \hat{a}(n)e^{-j2\pi f_{ALT}Tn}}$$

where: $\sigma^2 = c(0,0) + \sum_{n=1}^{P} \hat{a}(n)c(0,n)$

For a more detailed discussion of auto-regressive estimation, see *Modern Spectral Estimation: Theory and Applications*, by Steven Kay, Prentice Hall, 1988, pp. 222–225; incorporated herein by reference.

(e) Auto-Regressive Moving Average (ARMA) Estimation

Auto-Regressive Moving Average (ARMA) Estimation is yet another dynamic method which may be substituted for complex demodulation. ARMA estimation involves modeling the alternans with a data sequence X(n) as follows:

$$X(n) = -\sum_{k=1}^{P} [a(k) \times X(n-k)] + \sum_{k=0}^{q} [b(k) \times u(n-k)]$$

Note that this equation is similar to the model of X(n) according to the AR method, however, additional coefficients "b(k)" have been added to the model. These coefficients are necessary when the spectrum of the data has contours which are more complex than just spikes due to alternans and respiration periodicities. Let "â" and " " be the best estimates of "a" and "b". The auto regressive coefficient estimates are found by performing Newton Raphson Iteration to find the zeros of:

$$\left[\left(\frac{\delta Q}{\delta a}\right)^T + \left(\frac{\delta Q}{\delta b}\right)^T\right]^T$$

This minimizes the error function:

$$Q(a,b) = \int_{-\frac{1}{2}}^{\frac{1}{2}} I(f) \frac{|A(f)|^2}{|B(f)|^2} df$$

where:

$$I(f) = \frac{1}{M}\left|\sum_{n=0}^{M-1} X(n)e^{-j2\pi fn}\right|^2$$

$$A(f) = 1 - \sum_{k=1}^{q} a(k)e^{-j2\pi fk}$$

$$B(f) = \sum_{k=0}^{P} b(k)e^{-j2\pi fk}$$

The estimate of the alternans magnitude is then given by:

$$A(n) = \frac{\sigma^2 \sum_{k=1}^{q} b(k)e^{-j2\pi f_{ALT}Tk}}{1 - \sum_{k=1}^{P} a(k)e^{-j2\pi f_{ALT}Tk}}$$

where: $\sigma^2 = Q(a,b)$

For a more detailed discussion of auto-regressive moving average estimation, see *Modern Spectral Estima-*

*tion: Theory and Applications*, by Steven Kay, Prentice Hall, 1988, pp. 309-312; incorporated herein by reference.

The resultant time series A(n), representative of the magnitude of alternans, which is produced in step 318 (by one of the dynamic methods set forth above) may then be analyzed for diagnostic purposes. This may include producing a surface plot as shown in FIGS. 11(a)-(c) (described below).

It will be understood by one skilled in the art that the various steps of filtering set forth above may be performed by analog or digital means as discussed below. It will further be understood that each of the various filtering steps may be modified or eliminated from the method, if desired. Note, however, that detrending is particularly important for the Least Squares Estimate Method.

Elimination of the various filtering steps will, of course, lead to a reduction in clarity and will add corruption to the sought after signals. The amount of corruption will depend on the amount of noise present in the specific data. The noise sources sought to be filtered include: white noise, respiration induced electrical activity, premature beats, slowly varying trends present in the area under the ECG waveforms, and other miscellaneous noises.

Apparatus of the Invention

The preferred embodiment of the apparatus is described with reference to FIGS. 4-7. Steps 204-208 of the method may be performed using a conventional ECG machine or may be performed using dedicated hardware. Similarly, steps 212 and 214 may be performed on a general purpose computer or may performed by dedicated hardware.

In the preferred embodiment, the invention is carried out on an alternans monitoring unit (AMU) 400. AMU 400 includes ECG sensing leads 401, an ECG detector and pre-processor 402 and an ECG processing system 404. ECG detector and pre-processor 402, shown in greater detail in FIG. 5, includes a high-pass filter 502, a pre-amplifier 504, and a low-pass filter 506. ECG sensing leads (i.e., electrodes) 401 provide a signal from a patient directly to high-pass filter 502.

In an alternate embodiment, ECG detector and pre-processor 402 is a conventional ECG monitoring machine.

Figure 6:
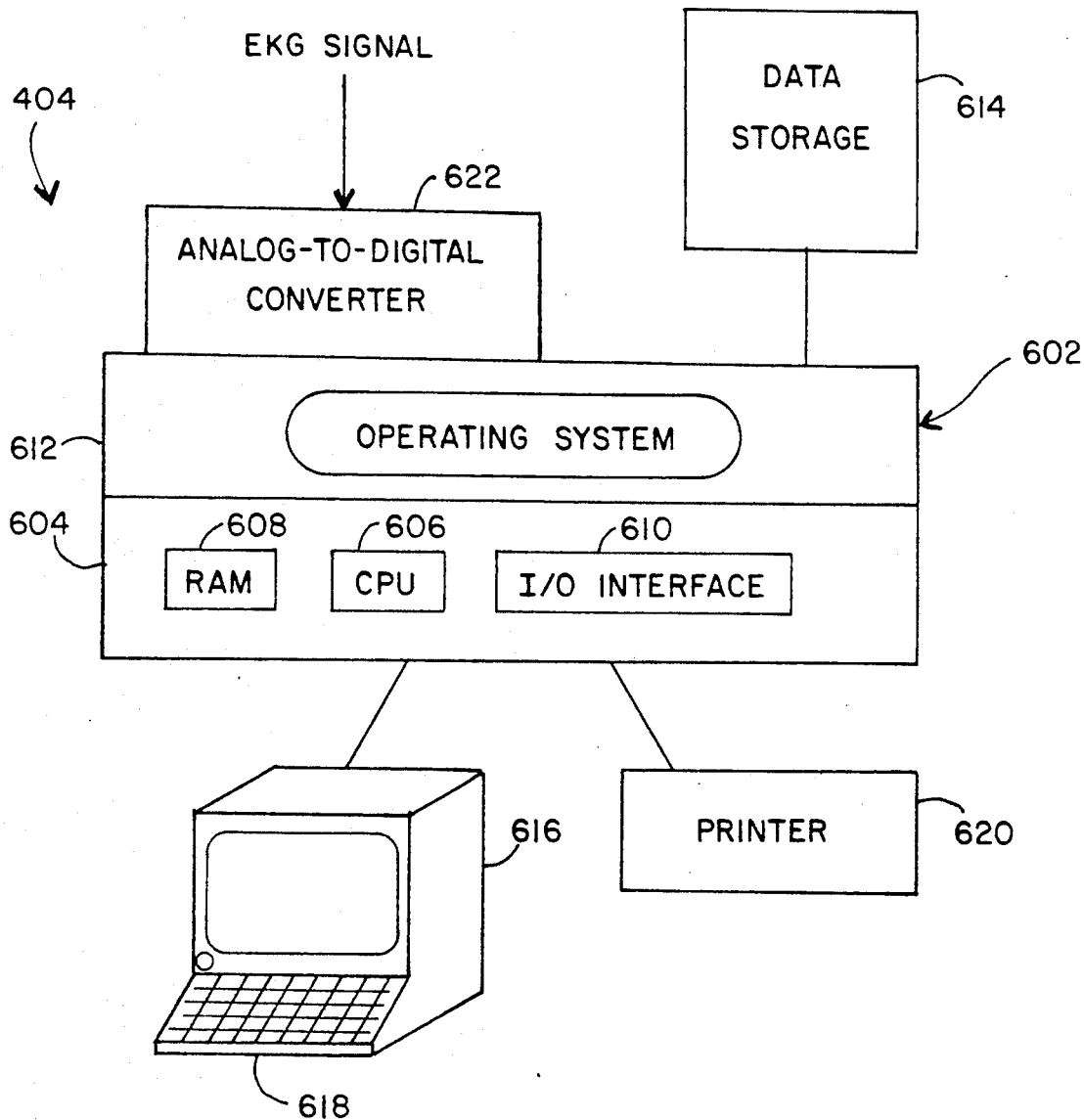
FIG. 6 is a detailed block diagram of ECG processing system 404 comprising a microcomputer.

Referring now to FIG. 6, ECG processing system 404 is described. ECG processing system 404 includes a programmed microcomputer 602 equipped with an analog-to-digital (A/D) conversion board 622. The steps of the method are performed using a software program written in C Programming language. The program follows the steps set forth above. It is believed that any skilled programmer would have no difficulty writing the code necessary to perform the steps of this invention.

Microcomputer or computer platform 602 includes a hardware unit 604 which includes a central processing unit (CPU) 606, a random access memory (RAM) 608 and an input/output interface 610. RAM 608 is also called a main memory. Computer platform 602 also typically includes an operating system 612. In addition, a data storage device 614 may be included. Storage device 614 may include an optical disk or a magnetic tape drive or disk.

Various peripheral components may be connected to computer platform 602, such as a terminal 616, a keyboard 618, and a printer 620. Analog-to-digital (A/D) converter 622 is used to sample an ECG signal. A/D converter 622 may also provide amplification of the ECG signal prior to sampling.

Figure 7:
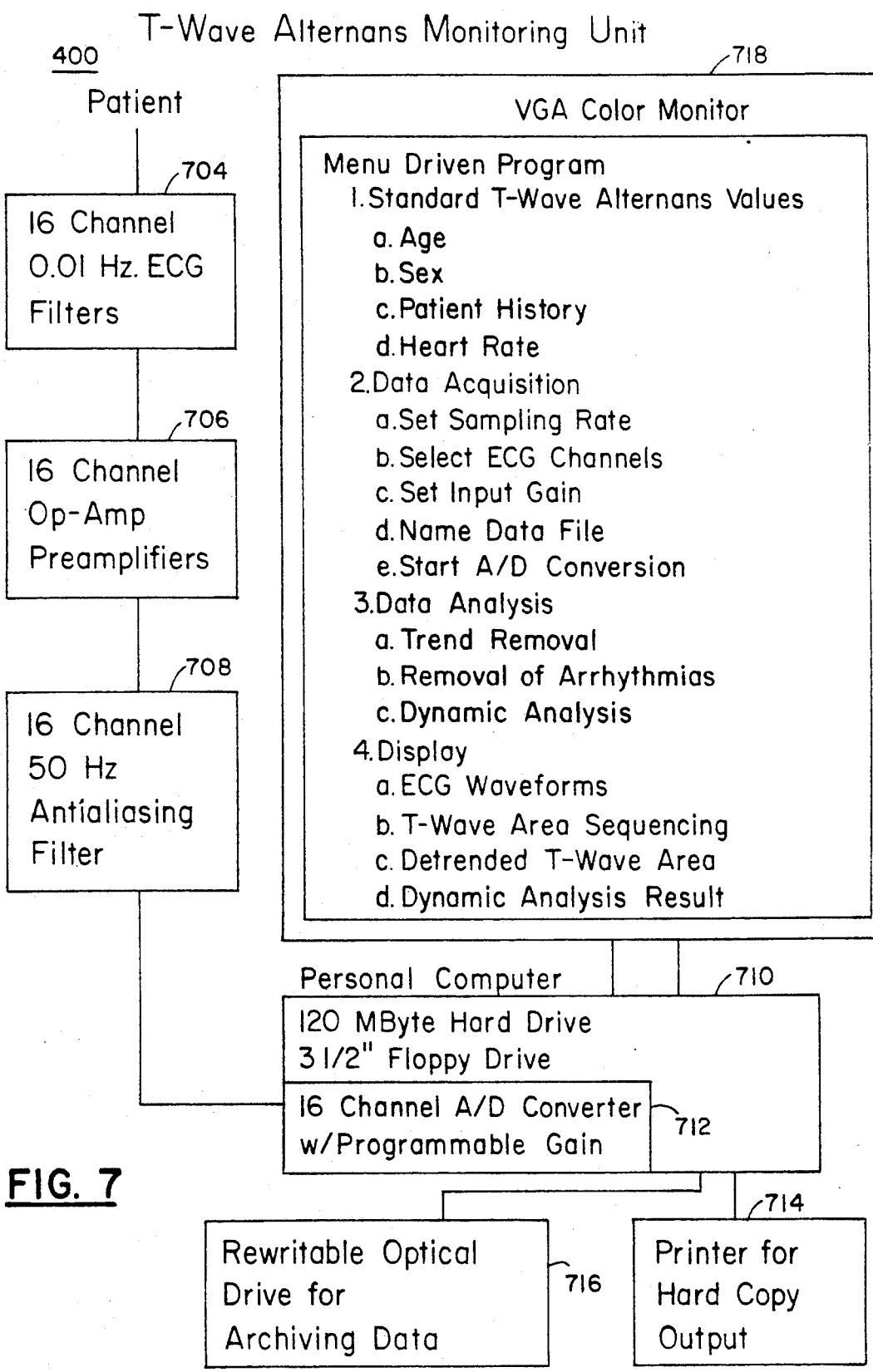
FIG. 7 is a detailed block diagram of the preferred embodiment of T-wave alternans monitoring unit (AMU) 400.

FIG. 7 shows the preferred embodiment of AMU 400. The system includes 16 channels to allow simultaneous monitoring of a plurality of ECG leads. High-pass filters 704, pre-amplifiers 706, and low-pass filters 708 perform steps 204, 206 and 208, respectively. High-pass filters 704 have a 0.01 Hz roll-on. Low-pass filters 708 have a 50 Hz bandwidth.

A personal computer 710 includes an A/D converter (with programmable gain), a printer 716, a re-writable optical disk 716, and a color monitor 718. The program which runs on computer 710 is preferably menu-driven. A sample menu is shown on monitor 718.

The menu-driven program may take, as input, information on a patient's age, sex, medical history, and heart rate. This information could then be used to select a range of standard T-wave alternans values to be used for comparison. The menu program would further allow the clinician/operator to select the A/D sampling rate, the number of ECG channels to monitor, and the gain of the A/D converter prior to commencing data collection. Thereafter, the clinician/operator could manually control removal of trends and premature beats prior to performing the dynamic analysis to estimate the amplitude of alternans.

Features of the menu-driven program may include selecting the method of dynamic analysis to be used and selecting the results to be displayed. For example, the clinician/operator may desire to view the ECG waveforms, the time series data for each bin of the T-wave (both before and after detrending), or the actual alternans estimate data.

Animal Study

Animal studies were conducted by the inventors at Georgetown University School of Medicine in Washington, D.C. Sixteen adult mongrel dogs (20 to 30 kg) of both sexes were studied in accordance with the standards of the scientific community. The animals were pre-medicated with morphine sulfate (2 mg/kg, subcutaneously) and anesthetized with alpha-chloralose (150 mg/kg, intravenously), with supplemental doses of alpha-chloralose (600 mg in 60 ml saline) as required. A left thoracotomy was performed via the fourth intercostal space.

A Doppler flow probe was placed around the left anterior descending (LAD) coronary artery and occlusions were performed using a 2-0 silk snare. Aortic blood pressure was measured with a Gould-Statham P50 pressure transducer. The ECG was obtained using a 7 French USCI quadripolar catheter with an inter-electrode distance of 10 mm and an electrode width of 2 mm. The catheter was positioned in the apex of the left ventricle via a carotid artery to coincide with the ischemia. This catheter placement was found to produce optimal ECG sensing.

Bipolar ECG's were obtained with the negative pole being the second electrode of the catheter and the positive pole being a needle-electrode placed transcutaneously in the lower left hip region. A pigtail pressure catheter was positioned to monitor left ventricular (LV) blood pressure. The area under the LV pressure pulse of successive beats was analyzed using the technique of complex demodulation. No evidence of mechanical alternans was found. The electrocardiographic and hemodynamic data were continuosly recorded on a Thorn EMI FM tape recorder (45 to 50 db S/N ratio, bandwidth of each channel 0 to 625 Hz). Arterial blood pH, $pCO_2$, and $pO_2$ were monitored using an Instrumentation Laboratory 1304 blood gas analyzer and were maintained within physiologic ranges by adjusting ventilation parameters of the Harvard respirator.

A bilateral stellectomy was performed to interrupt sympathetic neural input to the heart. This was accomplished by removal of the right stellate ganglion via the right second interspace and by sectioning the preganglionic fibers and the caudal end of the left ganglion through the left thoracotomy. The ansae subclavia were left intact to permit pacing of the heart at a rate of 150 beats per minute. Pacing was accomplished by delivering electrical stimuli of 1.5 to 2 mA of 5 ms duration at a frequency of 10 Hz to the nerves with a Grass S44 stimulator and an SIU7 stimulus isolation unit.

At the end of each experiment, the taped data was low-pass filtered to limit the signal bandwidth to 50 Hz. The data was then digitized at 500 samples per second, with a Compaq 386 computer equipped with a Metrabyte DAS-20 A/D conversion board, and stored on an optical disk. The apex of each R-wave for each of the N beats was then located by finding the peak amplitudes in the digitized signal. Each beat was indexed by n from 1 to N. The R-R interval was employed to sort out and remove premature beats which could introduce artifactual spikes.

The period from 60 to 290 ms following the apex of each R-wave was determined to coincide with the location of the T-wave. This period was divided into bins 10 ms wide for each successive beat, and the area between the ECG and the isoelectric baseline was computed for each 10 ms interval. N successive beats from control through release were then sequenced into a time series for each of the 23 10-ms bins: $(X(n), n=1,2, \ldots N)$. A sixteenth order Butterworth filter was used for both detrending and demodulating to remove the large low-frequency variation in T-wave area that occurs during occlusion and to leave a cleaner signal for spectral estimation.

Detrending was performed by low-pass filtering each time series with the Butterworth filter and then subtracting the result from the original time series to achieve a high-pass filtering function. To obtain estimates of the magnitude of beat-to-beat alternation in the amplitude of each of these twenty-three time series, complex demodulation (as set forth above) was used.

The effects of LAD coronary artery occlusion and reperfusion on T-wave alternans were tested before and after sympathetic denervation and stimulation. Baseline data was obtained for four minutes, the artery was occluded for eight minutes followed by abrupt release (reperfusion) and a 30-minute rest period. As set forth above, heart rate was maintained constant by atrial pacing at 150 bpm during assessment of the magnitude of alternans.

In eight dogs, a preconditioning occlusion was followed by a control occlusion with nerves intact. The occlusion-release sequence was repeated after stellate ganglion ablation. Finally, the left stellate ganglion was stimulated two to three minutes prior to occlusion, during the second and fifth minutes of occlusion, and during reperfusion. In the second group of eight dogs, the order of interventions was changed to rule out sequence-related error by omitting the occlusion with nerves intact.

FIGS. 8(a)-10(a) show, respectively, an electrocardiogram recorded within the left ventricle before, during, and after coronary artery occlusion in a single representative animal. FIGS. 8(b)-10(b) show superimposition of six successive beats. Prior to occlusion (FIG. 8), the T-waves of each succeeding beat are uniform. After four minutes of coronary artery occlusion (FIG. 9), there is marked alternation of the first half of the T-wave, coinciding with the vulnerable period of the cardiac cycle. The second half of the T-wave remains uniform. After release of the occlusion (FIG. 10), alternans is bidirectional, with T-waves alternately inscribed above and below the isoelectric line.

Coronary artery occlusion and reperfusion both resulted in significant increases in the magnitude of beat-to-beat alternation in T-wave amplitude. FIG. 11 shows a surface plot display derived by complex demodulation of the T-wave of the electrocardiogram before, during, and after coronary artery occlusion in eight dogs with intact cardiac innervation (FIG. 11(a)); after bilateral stellectomy in six dogs (FIG. 11(b)); and during 30 sec of stimulation of the ansa subclavia of the decentralized left stellate ganglion in eleven dogs (FIG. 11(c)).

The increase in alternans was evident within two to three minutes of occlusion and progressed until the occlusion was terminated at eight minutes. Upon reperfusion, there was an abrupt increase in alternans which lasted less than one minute. A remarkable feature is that the pattern of alternation during reperfusion was bidirectional, with T-waves occurring alternately above and below the isoelectric line (FIG. 10).

Figure 12:
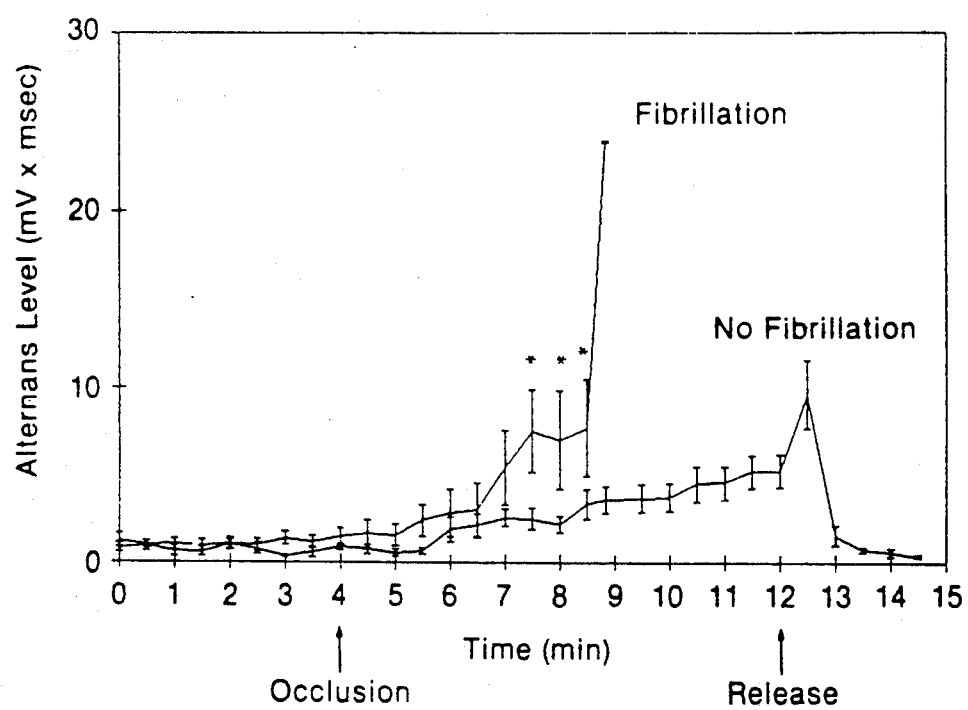
FIG. 12 shows the correlation between the occurrence of spontaneous ventricular fibrillation and T-wave alternans in ten dogs.

The time course of onset and offset of T-wave alternans during the occlusion-release sequence coincides with the spontaneous appearance of malignant tachyarrhythmias including ventricular fibrillation. FIG. 12 shows a correlation between the occurence of spontaneous ventricular fibrillation and T-wave alternans in ten dogs. Dogs which fibrillated exhibited a rapid rise in alternans within the first three or four minutes of occlusion and this change was significantly more marked than that observed in animals which survived the entire occlusion-release sequence (*=p<0.001. Values are means ±S.E.M.). The results were analyzed using a one-way ANOVA with Scheffé correction for multiple comparisons. In both groups, the control values did not differ significantly from the normal distribution by the Kolmogorov-Smirnov test.

It is noteworthy that alternans is marked, though short lasting, during reperfusion. This transient period of heightened vulnerability to fibrillation is thought to be due to liberation of washout products of cellular ischemia. The differing mechanisms responsible for vulnerability during occlusion and reperfusion may account for the contrasting alternation pattern in T-wave morphology.

The studies demonstrate that the sympathetic nervous system exerts a prominent effect on T-wave alternans, a finding which is consistent with its established arrhythmogenic influence. During coronary artery occlusion, stellectomy (FIG. 11(b)) reduced alternans during the early phase of occlusion [from 15.8±6.6 at 4 minutes during control to 4.7±1.0 mV ×ms (means ±S.E.M., p<0.05)], coinciding with the time when neural activity is high in intact animals. However, later in the occlusion, extra-adrenergic factors may play a role.

Sympathetic neural influences during the reperfusion phase also appear to be tracked reliably by the present techniques. It was observed that stellate ganglion ablation increased T-wave alternans during reperfusion [from 19.8±3.0 to 29.8±3.3 mV ×ms (p<0.02)]. This concurs with a previous study indicating that stellectomy enhances reperfusion-induced vulnerability to fibrillation. Stellate ganglion stimulation restored the magnitude of alternans to a value which was not statistically different from pre-denervation levels.

The link between alternans and vulnerability is underscored by the finding that alternans coincides with the established timing of the vulnerable period in the cardiac cycle. Superimposition of successive beats indicates that alternation is restricted to the first half of the T-wave (FIGS. 8(b)-10(b)). This relationship remained constant in all animals studied under the changing conditions of sympathetic nervous system stimulation or denervation.

Clinical Applicability

As discussed above, the inventors have discovered that positioning the ECG sensing electrode into the apex of the left ventricle produces an optimal ECG signal for sensing alternans. This intracavitary electrode placement, however, requires invasive and hazardous procedures such that its clinical, diagnostic applicability is limited. What is needed is a method for sensing T-wave alternans non-invasively on the surface of the body.

Before discussing sensing of the electrical activity of the heart, it is helpful to understand a few basic principles. The electrical signals that are sensed as an ECG include electrical currents that flow through the body as a result of depolarization and repolarization of the myocardial cells. This electrical activity may be sensed as a voltage between areas of the body (e.g., between the chest proximate the heart and an arm or leg).

Theoretically, the voltage "V" at a position $(x_p,y_p,z_p)$ due to a charge "q" at $(x_i,y_j,z_k)$ is given by the following equation:

$$V = \frac{q}{4\pi\epsilon \sqrt{(x_p - x_i)^2 + (y_p - y_j)^2 + (z_p - z_k)^2}} - V_{ref}$$

where: $\epsilon$=permitivity constant

It is assumed that $V_{ref}$ is zero for a unipolar electrode, as discussed below. If the heart is modelled as a collection of charges then the equation directly below will approximate the voltage $V_{norm}$ sensed by an electrode located at a point $(x_p,y_p,z_p)$.

$$V_{norm} = \sum_i \sum_j \sum_k \frac{q}{4\pi\epsilon \sqrt{(x_p - x_i)^2 + (y_p - y_j)^2 + (z_p - z_k)^2}}$$

Under stable repolarization/depolarization, the charges of the heart will repeat almost identically to create a stable ECG signal. That is, the charge distribution occurring x msec after the R-wave of one cardiac cycle will be nearly identical to the charge distribution occurring x msec after the R-wave of the next cardiac cycle.

When alternans is present, however, the charge distribution will be modulated such that the charge distribution occurring x msec after the R-wave of successive cardiac cycles can be modeled as a static charge distribution plus a time varying distribution representing the source of the alternans. This time varying charge distribution resulting from alternans may be represented by:

$$q_{alternans} = q \cos(2\pi f_{ALT} t)$$

where:
q = the magnitude of the alternating charge
$f_{ALT}$ = alternation frequency (Hz)
t = 0, 1, 2, ... number of beats Locating the alternans charge at (0,0,0) produces an oscillating voltage at $(x_p,y_p,z_p)$ as follows:

$$V_{alternans} = \frac{q \cos(2\pi f_0 t)}{4\pi\epsilon \sqrt{x_p^2 + y_p^2 + z_p^2}}$$

where:
$V_{alternans}$ = the magnitude of the alternans voltage measured at a point $(x_p,y_p,z_p)$ This results in a total voltage at point $(x_p,y_p,z_p)$ of:

$$V_{total} = V_{norm} + V_{alternans}$$

$V_{total}$ consists of an alternating component plus a constant component. To maximize the amount of alternating component detected, $(x_p,y_p,z_p)$ must approach (0,0,0). That is, the detecting electrode must be located as close as possible to the portion of the heart that is generating the alternation signal.

For sensing a normal ECG, limb leads, such as lead II (left leg with respect to right arm) can be used. Limb leads, however, are incapable of detecting the small amplitudes of alternans. Interestingly, the inventors have discovered that alternans is a regional phenomenon that can be reliably detected via the precordial ECG leads.

By regional, it is meant that the alternans emanate from the injured or ischemic portion of the heart. For example, it was found that the alternation signal is strongest in the left ventricle (LV) intracavitary ECG during a left anterior descending (LAD) coronary artery occlusion. In fact, it was noted that alternation is twelve times greater as recorded from a LV intracavitary catheter as compared with a right ventricle (RV) intracavitary catheter. Corresponding to this discovery, the inventors have found that alternans could be detected in the precordial surface ECG leads corresponding to the injured portion of the heart. Note that the terms "lead" and "electrode" are used interchangeably herein.

The precordial or chest leads are unipolar electrodes which sense the ECG signal at the surface of the body. A unipolar electrode senses a positive electrical current with respect to a neutral lead. The neutral lead is an average of the voltage on the three standard limb leads: left leg, left arm, and right arm. Ideally, the voltage on the neutral lead is zero.

Figure 13A:
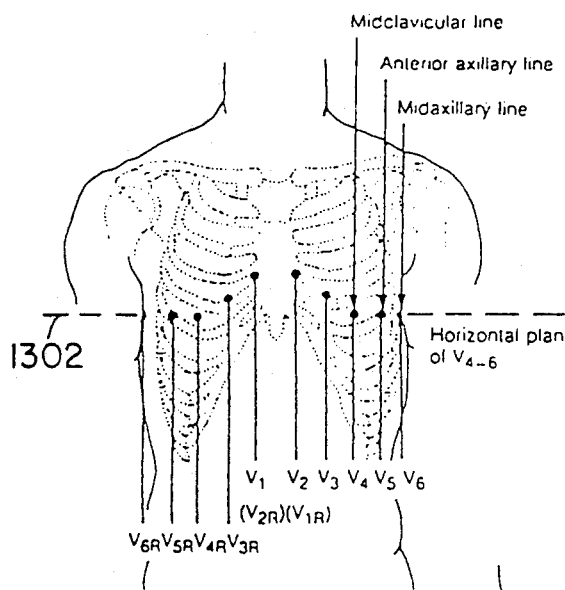
FIGS. 13(a)-(c) illustrate the positioning of the precordial ECG leads on the body.
Figure 13B:
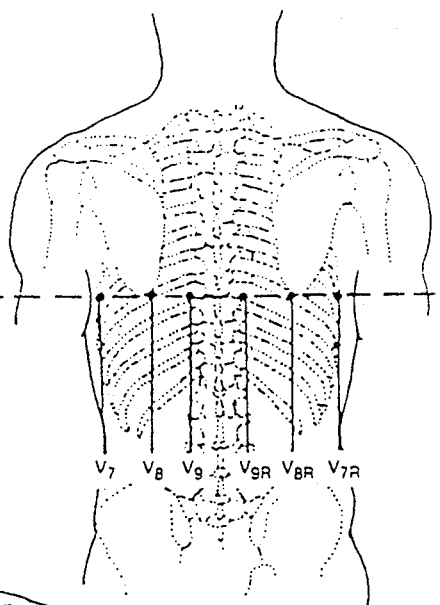
Figure 13C:
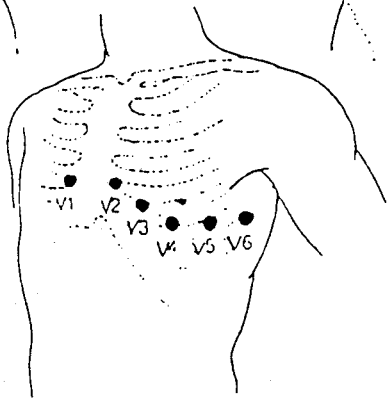

The location of the precordial leads on the body surface are shown in FIGS. 13(a)-(c). The precordial leads include leads $V_1$ through $V_9$ for the left-hand side of the body and lead $V_{1R}$ through $V_{9R}$ for the right-hand side of the body. Note that lead $V_1$ is the same as lead $V_{2R}$ and that lead $V_2$ is the same as lead $V_{1R}$.

Figure 14:
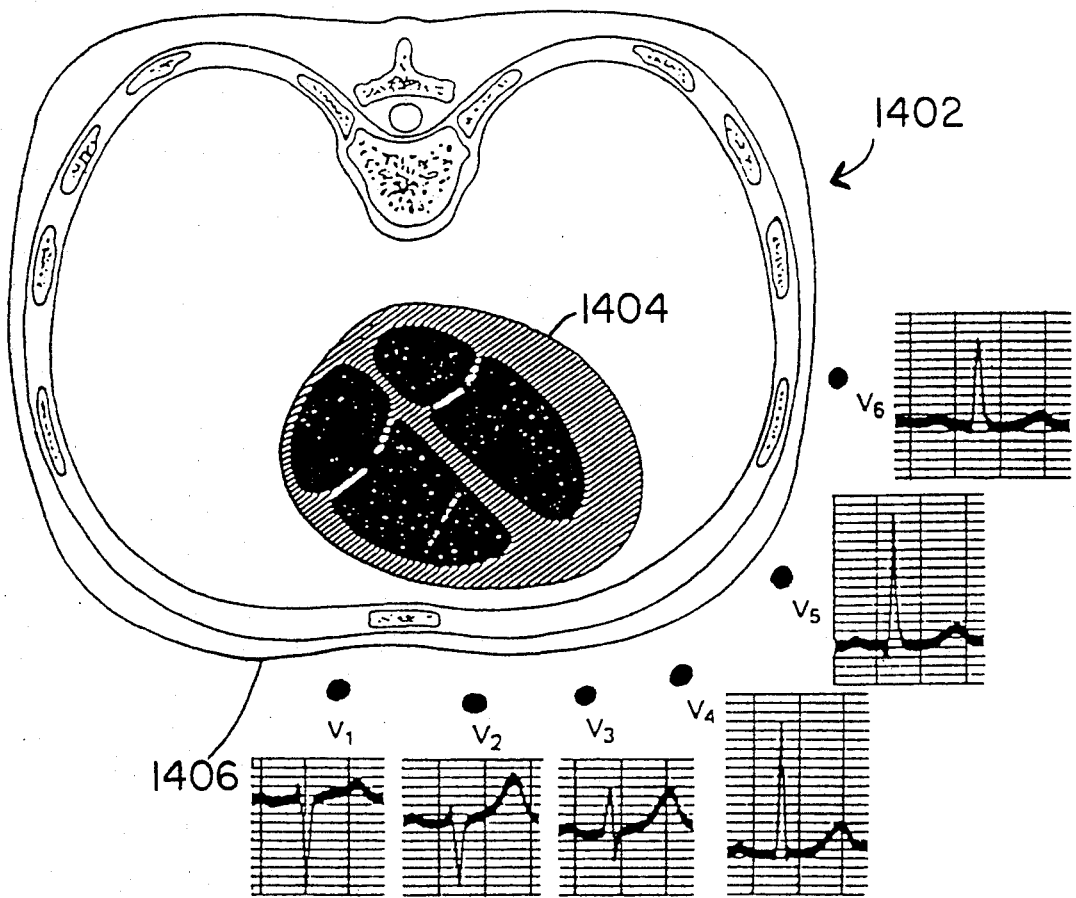
FIG. 14 is a cross-section of the human body illustrating the positioning of precordial ECG leads $V_1$-$V_6$ relative to the heart.
Figure 15A:
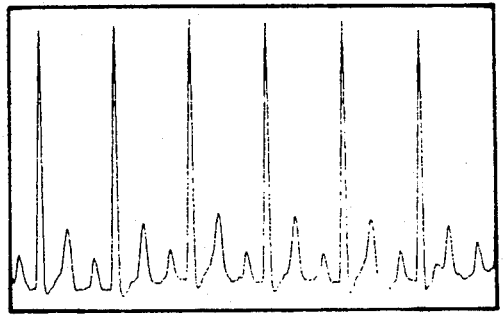
FIG. 15(a) is an ECG recorded from lead II during coronary artery occlusion in a dog.
Figure 15B:
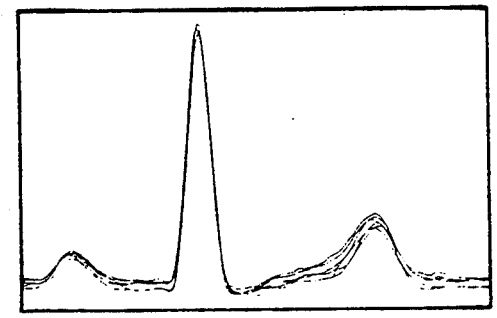
FIG. 15(b) shows superimposition of six successive beats from FIG. 15(a) presented on an expanded time scale.
Figure 16A:
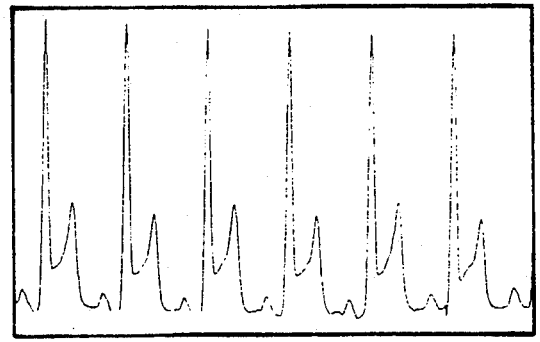
FIG. 16(a) is an ECG from precordial lead $V_5$ recorded simultaneously with the ECG of FIG. 15(a).
Figure 16B:
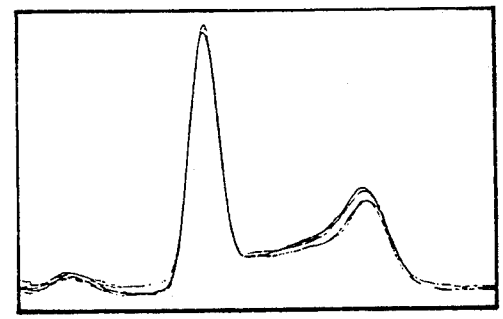
FIG. 16(b) shows superimposition of six successive beats from FIG. 16(a) presented on an expanded time scale.
Figure 17A:
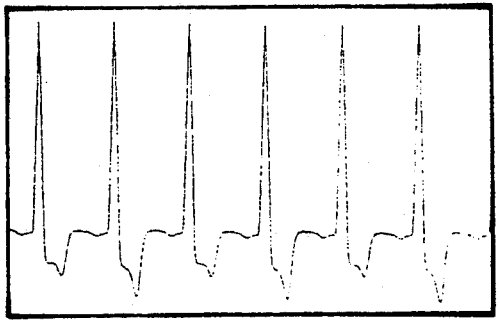
FIG. 17(a) is an ECG from a left ventricular intracavitary electrode recorded simultaneously with the ECG of FIG. 15(a).
Figure 17B:
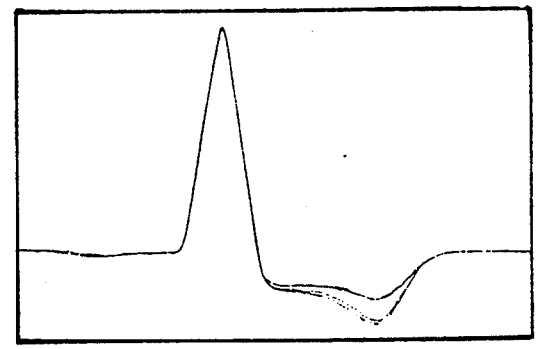
FIG. 17(b) shows superimposition of six successive beats from FIG. 17(a) presented on an expanded time scale.

The present invention is concerned primarily with precordial leads $V_1$ through $V_6$ because they are closest to the heart and, therefore, yield the strongest ECG signals. FIG. 14 is a cross-sectional view of the human chest area 1402 taken along a horizontal axis 1302 shown in FIGS. 13(a) and 13(b). FIG. 14 illustrates the position of the heart 1404 in relation to front chest wall 1406. The relative positions of precordial leads $V_1$ through $V_6$ and the corresponding normal ECG signals present at each position are also shown. Note that lead $V_5$ resides directly over the left ventricular surface.

The inventors have discovered that leads $V_5$ and/or $V_6$ are optimal for sensing alternans which result from injury to the left ventricle (e.g., obstruction of the left anterior descending artery), and leads $V_1$ and/or $V_2$ are optimal for sensing injuries such as obstruction of the right-side coronary circulation. Additional precordial leads, such as $V_9$, may be useful for sensing alternans resulting from remote posterior wall injury. Thus, a physician may use the complete precordial lead system to obtain precise information regarding the locus of ischemia or injury.

In order to achieve the maximum sensitivity for alternans sensing, attenuation by the skin and other body tissues must be reduced. Attenuation by the relatively large impedance provided by the skin can be overcome by proper skin abrasion, electrode jelly, or the use of needle electrodes. Further reduction in attenuation can be achieved by selecting the path of least resistance to the heart. This includes placing the electrodes between the ribs rather than over them.

FIGS. 15(a)-17(a) show continuous ECG tracings obtained simultaneously from lead II, lead $V_5$, and a left ventricular intracavitary lead, respectively, during left anterior coronary artery occlusion in a chloralose-anesthetized dog. FIGS. 15(b)-17(b) show superimposition of the successive beats of FIGS. 15(a)-17(a), respectively. Note that the superimposed waveform from lead II [FIG. 15(b)] shows no consistently detectable alternans. Lead $V_5$ [FIG. 16(b)], however, shows marked alternation in the first half of the T-wave, corresponding to the alternation observed in the intracavitary lead [FIG. 17(b)].

Figure 18:
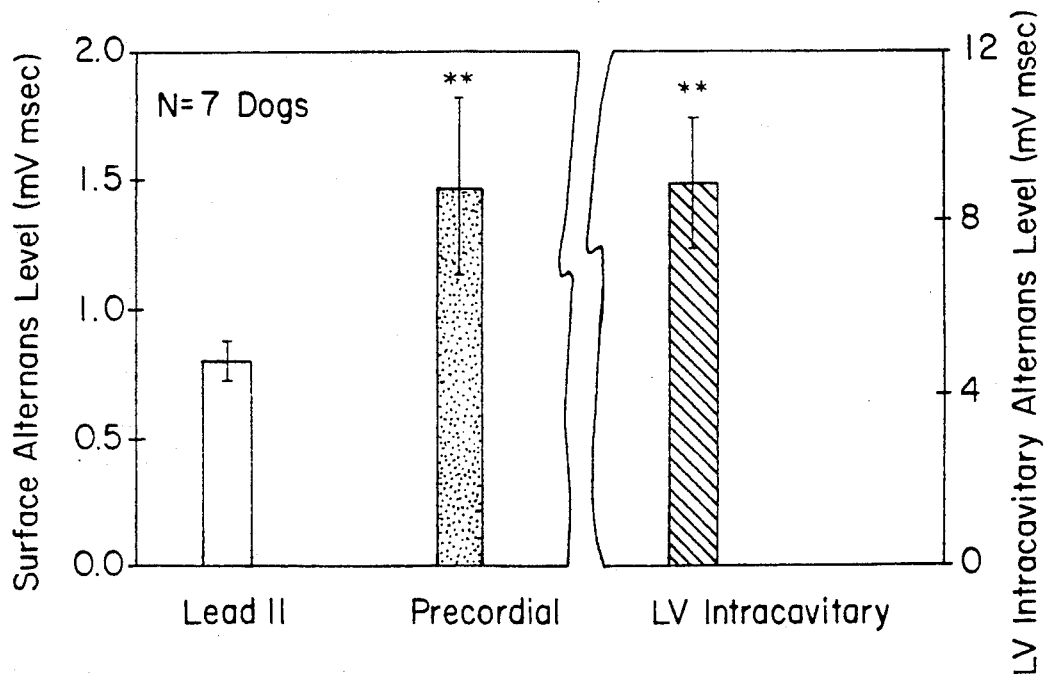
FIG. 18 is a bar graph showing the relative magnitudes of alternans signals sensed from lead II, from precordial lead $V_5$, and from a left ventricular intracavitary electrode.

Simultaneous comparison of T-wave alternation from lead II, lead $V_5$, and a left ventricular intracavitary lead during left anterior coronary artery occlusion in seven dogs was performed. The results are shown graphically in FIG. 18 as a comparison of the relative amplitudes of alternans energy from each lead. As shown, the signal from lead $V_5$ is clearly larger than that of lead II. The intracavitary lead provides a stronger signal than both lead II and $V_5$; however, lead $V_5$ obviates the need to place a catheter within the heart.

Under certain clinical conditions, it may be advantageous to record alternation from the right ventricle (RV) because of the nature of the cardiac pathology. For example, under conditions of right heart hypertrophy or other pathology, or right coronary artery disease, the maximum expression of alternation may be detectable from a catheter positioned in the RV. Since a catheter can be positioned from the venous side of the circulation, the RV catheterization is relatively low risk and routine.

Conclusion

The ability to sense alternans non-invasively from a surface ECG via the precordial leads and to track the alternans dynamically yields a diagnostic tool of unprecedented value in the field of cardiology. The inventors contemplate producing a standard T-wave alternans index which relates to a patients age, sex, medical history, and heart rate. Monitored values of alternans could then be compared to this standard index to yield diagnostic information on cardiac health. This includes detecting and locating ischemic or injured portions of the heart. Because of the regional nature of alternans, comparison of the alternans from each precordial lead with a corresponding standard index value for that lead would allow an ischemic or injured site to be located without the need for invasive procedures.

The alternans monitoring unit could further be miniaturized and incorporated into an implantable cardioverter/defibrillator unit to sense alternans and then deliver drugs or electricity to prevent or abort life-threatening rhythms or to revert cardiac arrest.

Although the invention has been described and illustrated with a certain degree of particularity, it is understood that those skilled in the art will recognize a variety of applications and appropriate modifications within the spirit of the invention and the scope of the claims.

What is claimed is:

1. A method of analyzing an ECG having a plurality of R-R intervals for dynamic tracking of cardiac vulnerability, comprising the steps of:
   sampling said ECG signal;
   predicting the location in said ECG signal of the T-wave in each R-R interval;
   partitioning each T-wave in said ECG signal into a plurality of time divisions;
   summing the samples in each of said time divisions of said ECG signal;
   forming a time series for each of said time divisions, each time series including corresponding sums from corresponding time divisions from successive ones of said T-waves; and
   performing dynamic estimation on each said time series to estimate the amplitude of beat-to-beat alternation for each said time division.

2. The method of claim 1, wherein said step of performing dynamic estimation includes performing complex demodulation on each said time series.

3. The method of claim 1, wherein said step of performing dynamic estimation includes performing estimation by subtraction on each said time series.

4. The method of claim 1, wherein said step of performing dynamic estimation includes performing least squares estimation on each said time series.

5. The method of claim 1, wherein said step of performing dynamic estimation includes performing autoregressive estimation on each said time series.

6. The method of claim 1, wherein said step of performing dynamic estimation includes performing autoregressive moving average estimation on each said time series.

7. The method of any of claims 1-6, further comprising the step of detrending each said time series prior to performing dynamic estimation in order to eliminate the effects of drift and DC bias.

8. The method of any of claim 7, further comprising the step of comparing each R-R interval with a standard criteria to eliminate premature beats.

9. The method of claim 8, wherein predicting the location in said ECG signal of the T-wave in each R-R interval includes identifying in said ECG signal the location of the R-wave in each R-R interval and predicting the location of the T-wave with respect to the location of the R-wave.

10. A method for dynamic tracking of cardiac vulnerability, comprising the steps of:
    sensing an ECG signal from a heart, said ECG signal having a plurality of R-R intervals, each R-R interval including an R-wave and a T-wave;

sampling said ECG signal;

predicting the location in said ECG signal of the T-wave in each R-R interval;

partitioning each T-wave in said ECG signal into a plurality of time divisions;

summing the samples in each of said time divisions of said ECG signal;

forming a time series for each of said time divisions, each time series including corresponding sums from corresponding time divisions from successive ones of said T-waves; and performing dynamic estimation on each said time series to estimate the amplitude of beat-to-beat alternation for each said time division.

11. The method of claim 10, wherein said step of performing dynamic estimation includes performing complex demodulation on each said time series.

12. The method of claim 10, wherein said step of performing dynamic estimation includes performing estimation by subtraction on each said time series.

13. The method of claim 10, wherein said step of performing dynamic estimation includes performing least squares estimation on each said time series.

14. The method of claim 10, wherein said step of performing dynamic estimation includes performing auto-regressive estimation on each said time series.

15. The method of claim 10, wherein said step of performing dynamic estimation includes performing auto-regressive moving average estimation on each said time series.

16. The method of any of claim 10-15, further comprising the step of detrending each said time series prior to performing dynamic estimation in order to eliminate the effects of drift and DC bias.

17. The method of any of claim 16, further comprising the step of comparing each R-R interval with a standard criteria to eliminate premature beats.

18. The method of claim 17, wherein predicting the location in said ECG signal of the T-wave in each R-R interval includes identifying in said ECG signal the location of the R-wave in each R-R interval and predicting the location of the T-wave with respect to the location of the R-wave.

19. The method of any of claims 10-15 wherein said ECG signal is sensed via a precordial surface lead.

20. The method of claim 18, wherein said ECG signal is sensed via a precordial surface lead.

21. A method for non-invasive, dynamic tracking of cardiac vulnerability in a live subject, comprising the steps of:

(a) placing a precordial ECG lead on the surface of the subject's body proximate to the subject's heart to sense an ECG signal, said ECG signal having a plurality of R-R intervals, each R-R interval including an R-wave and a T-wave;

(b) amplifying said ECG signal;

(c) low-pass filtering said ECG signal;

(d) sampling said ECG signal;

(e) identifying in said ECG signal the location of the R-wave in each R-R interval;

(f) comparing each R-R interval with a standard criteria to eliminate premature beats;

(g) predicting the location in said ECG signal of the T-wave in each R-R interval;

(h) partitioning each T-wave in said ECG signal into a plurality of time divisions;

(i) summing the sampled ECG signal in each of said time divisions;

(j) forming a time series for each of said time divisions, each time series including corresponding sums from corresponding time divisions from successive ones of said T-waves;

(k) detrending each said time series; and (l) performing dynamic estimation of the amplitude of beat-to-beat alternation for each said time division on each detrended time series.

22. The method of 21, wherein said precordial ECG lead of step (a) is lead $V_5$ when alternans originate from the left-hand side of the heart and wherein said precordial ECG lead is lead $V_2$ when alternans originate for the right-hand side of the heart.

23. An apparatus for dynamically tracking cardiac vulnerability by analyzing alternans in the T-waves of a plurality of R-R intervals of an ECG, said apparatus comprising:

means for sampling the ECG;

means for predicting the location in the ECG signal of the T-wave in each R-R interval;

means for partitioning each T-wave in said ECG signal into a plurality of time divisions;

means for summing the samples of the ECG signal in each of said time divisions and for forming a time series for each of said time divisions, each time series including corresponding sums from corresponding time divisions from successive ones of said T-waves; and means for performing dynamic estimation on each time series to estimate the amplitude of alternation for each time division.

24. The apparatus of claim 23, further comprising means for detrending each said time series prior to performing dynamic estimation in order to eliminate the effects of drift and DC bias.

25. The apparatus of claim 24, further comprising means for comparing each R-R interval with a standard criteria to eliminate premature beats.

26. An apparatus for the non-invasive, dynamic tracking of cardiac vulnerability through analysis of alternans in the T-waves of an ECG signal, said ECG signal having a plurality of R-to-R intervals, said apparatus comprising:

means for non-invasively sensing the ECG signal from a living subject;

means for high-pass filtering the ECG signal to eliminate DC components;

means for amplifying the ECG signal;

means for low-pass filtering the ECG signal to eliminate noise;

means for sampling the ECG signal to produce a sampled ECG signal;

means for predicting the location in the sampled ECG signal of the T-wave in each R-R interval;

means for partitioning each T-wave in said sampled ECG signal into a plurality of time divisions;

means for summing the samples of the ECG signal in each of said time divisions and for forming a time series for each of said time divisions, each time series including corresponding sums from corresponding time divisions from successive ones of said T-waves; and means for performing dynamic estimation on each time series to estimate the amplitude of alternation for each time division.

27. The apparatus of claim 26, further comprising means for detrending each said time series prior to performing dynamic estimation in order to eliminate the effects of drift and DC bias.

28. The apparatus of claim 27, further comprising means for comparing each R-R interval with a standard criteria to eliminate premature beats.

* * * * *